United States Patent [19]

Constansa et al.

[11] Patent Number: 4,797,482
[45] Date of Patent: Jan. 10, 1989

[54] PROCESS FOR THE PREPARATION OF OXAZINOBENZOTHIAZINE 6,6-DIOXIDE DERIVATIVES

[75] Inventors: Jordi F. Constansa; Augusto C. Pinol; Juan P. Corominas, all of Barcelone, Spain

[73] Assignee: Provesan S.A., Geneva, Switzerland

[21] Appl. No.: 39,518

[22] Filed: Apr. 15, 1987

[30] Foreign Application Priority Data

Apr. 15, 1986 [FR] France .................. 86 05377

[51] Int. Cl.$^4$ .................. C07D 498/04; C07D 513/04
[52] U.S. Cl. .................. 544/33
[58] Field of Search .................. 544/33

[56] References Cited

FOREIGN PATENT DOCUMENTS 3521722 12/1985 Fed. Rep. of Germany .
2528433 12/1983 France .

*Primary Examiner*—John M. Ford
*Attorney, Agent, or Firm*—Blakely, Sokoloff, Taylor & Zafman

[57] ABSTRACT

The present invention relates to a process for the preparation of a 5-methyl-3-heteroaryl-2H,5H-1,3-oxazino[5,6-c] [1,2] benzothiazine-2,4-(3H)-dione 6,6-dioxide of the general formula I:

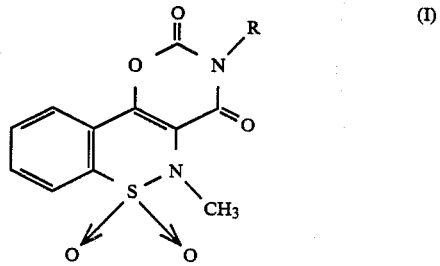

in which R represents a heteroaryl radical, preferably substituted or unsubstituted pyrimidinyl or pyridyl, of the type consisting in reacting an amide of the general formula II:

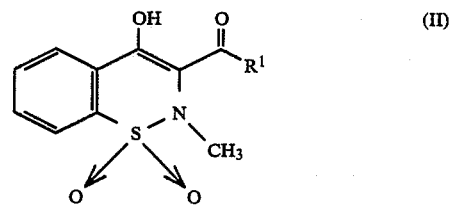

in which $R^1$ represents a heteroarylamino radical, preferably substituted or unsubstituted pyrimidinylamino or pyridylamino, with a compound of the general formula III:

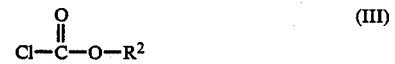

in which $R^2$ represents a $C_1$ to $C_4$ lower alkyl radical such as methyl or ethyl, an aryl radical such as phenyl, or an alkylaryl radical such as benzyl, wherein the reaction is carried out in an organic solvent selected from the group comprising pyridine, substituted pyridines such as 4-dimethylaminopyridine, 4-(pyrrolidin-1-yl)pyridine and 2,6-ditert.-butyl-4-methylpyridine, and mixtures thereof.

7 Claims, No Drawings

PROCESS FOR THE PREPARATION OF OXAZINOBENZOTHIAZINE 6,6-DIOXIDE DERIVATIVES

The present invention relates to a process for the preparation of 5-methyl-3-heteroaryl-2H,5H-1,3-oxazino[5,6-c][1,2]benzothiazine-2,4-(3H)-dione 6,6-dioxide derivatives corresponding to the general formula I below, which are obtained in excellent yield and in very pure form:

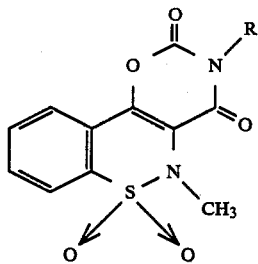

The oxazinobenzothiazine 6,6-dioxides of the general formula I, in which R represents a heteroaryl radical, preferably substituted or unsubstituted pyrimidinyl or pyridyl, are well-known antiinflammatories and analgesics, particularly droxicam, and are described in Chem. Abst., 1984, 100, 191893j.

In the prior art cited previously, oxazinobenzothiazine 6,6-dioxides were prepared from an ester of the general formula II:

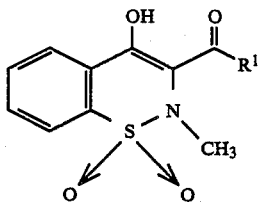

in which $R^1$ represents an alkoxy radical, such as methoxy or ethoxy.

Moreover, French Patent document No. A-2 566 408 describes the preparaion of 5-methyl-3-(pyridin-2-yl)-2H,5H-1,3-oxazino[5,6-c]-1,2-benzothiazine-2,4-(3H)-dione 6,6-dioxide from a compound of the formula II in which $R^1$ represents the pyridin-2-ylamino radical by reaction with phosgene in the presence of an organic solvent which is inert under the reaction conditions, and in the presence of an acid acceptor. Because of the economics of the process, and in order to obtain the best yield, the organic solvent preferably consists of methylene chloride, and triethylamine is used as the acid acceptor. A process of this type has serious disadvantages, however, especially when it is carried out on the industrial scale. First of all, it involves the use of phosgene, which is a highly toxic reagent; secondly, the yield it produces is much too low (56%).

The present invention relates to a novel process for the preparation of the derivatives of the general formula I defined above, which in fact makes it possible to eliminate the above-mentioned disadvantages. According to the invention, the derivatives of the general formula I are prepared by reacting an amide of the general formula II in which $R^1$ represents a heteroarylamino radical, preferably substituted or unsubstituted pyrimidinylamino or pyridylamino, with a compound of the general formula III:

in which $R^2$ represents a $C_1$ to $C_4$ lower alkyl radical such as methyl or ethyl, an aryl radical such as phenyl, or an alkylaryl radical such as benzyl.

The reaction between the compounds of the general formulae II and III takes place at temperatures of between about $-5°$ C. and about $50°$ C. for a period of approximately 3 hours to 48 hours.

According to the essential feature of the process of the present invention, the reaction between these two compounds takes place in an organic solvent selected from the group comprising pyridine, substituted pyridines such as 4-dimethylaminopyridine, 4-(pyrrolidin-1-yl)pyridine and 2,6-ditert.-butyl-4-methylpyridine, and mixtures thereof. When the solvent used is a mixture of pyridine and substituted pyridines, the latter will be used in a small proportion by weight, for example of 1 to 10%.

According to the present invention, this procedure affords derivatives of the general formula I with a very high degree of purity. These derivatives are moreover obtained by a process which is very simple to carry out on the industrial scale and leads to a very high yield of more than 90%.

The preparation of a few derivatives of the general formula I is described in detail in Examples 1 to 4, simply by way of a non-limiting illustration.

EXAMPLE 1

Preparation of 5-methyl-3-(pyridin-2-yl)-2H,5H-1,3-oxazino[5,6-c][1,2]benzothiazine-2,4-(3H)-dione 6,6-dioxide 13.8 liters (144 mol) of ethyl chloroformate are added dropwise to a partial solution of 11.9 kg (36 mol) of N-(pyridin-2-yl)-4-hydroxy-2-methyl-2H-1,2-benzothiazine-3-carboxamide 1,1-dioxide in 30 liters of anhydrous pyridine, with stirring and with cooling in an ice bath, in such a way that the temperature is always below 18° C. The mixture is stirred for 24 hours at room temperature and the whole of it is then poured into 175 liters of a water/ice mixture. After filtration, the residue is washed with copious amounts of distilled water, then with 0.5N hydrochloric acid and finally once again with distilled water. The residue is dissolved in acetone, from which 11.62 kg (90.5%) of 5-methyl-3-(pyridin-2-yl)-2H,5H-1,3-oxazino[5,6-c]-[1,2]benzothiazine-2,4-(3H)-dione 6,6-dioxide crystallize with a melting point of 264°–266° C.

Spectroscopic data: IR (KBr): 1185; 1355; 1410, 1640; 1710; 1790 cm$^{-1}$. $^1$H NMR, δ, [DMSO-d$_6$]: 3.02 (s, 3H); 7.52 (m, 2H); 7.92 (m, 5H); 8.52 (d, 1H).

EXAMPLE 2

Preparation of 5-methyl-3-(pyrimidin-2-yl)-2H,5H-1,3-oxazino[5,6-c][1,2]benzothiazine-2,4-(3H)-dione 6,6-dioxide 13.6 g (0.04 mol) of benzyl chloroformate as a 50% solution in toluene are added dropwise to a partial solution of 3.32 g (0.01 mol) of N-(pyrimidin-2yl)-4-hydroxy-2-methyl-2H-1,2-benzothiazine-3-carboxamide 1,1-dioxide in 25 ml of anhydrous pyridine, with stirring and with cooling in an ice bath, in such a way that the temperature always remains below 10° C. The mixture is stirred for 8 hours at 30° C. and the whole of it is poured into 100 ml of a water/ice mixture. After filtration, the residue is washed with copious amounts of distilled water and then immediately stirred in acetone heated to the boil, and the mixture is filtered. This gives 3.3 g (92%) of 5-methyl-3-(pyrimidin-2-yl)-2H,5H-1,3-oxazino[5,6-c][1,2]benzothiazine-2,4-(3H)-dione 6,6-dioxide melting at 282°–284° C.

Spectroscopic data: IR (KBr): 1180; 1355; 1400; 1632; 1710; 1787 cm$^{-1}$. $^1$H NMR, δ, [DMSO-d$_6$]: 3.05 (s, 3H); 7.93 (m, 5H); 8.95 (d, 2H).

EXAMPLE 3

Preparation of
5-methyl-3-(4-methylpyridin-2-yl)-2H,5H-1,3-oxazino[5,6-c][1,2]benzothiazine-2,4-(3H)-dione 6,6-dioxide 5 ml (0.04 mol) of phenyl chloroformate are added dropwise to a partial solution of 3.45 g (0.01 mol) of N-(4-methylpyridin-2-yl)-4-hydroxy-2-methyl-2H-1,2-benzothiazine-3-carboxamide 1,1-dioxide in a mixture of 2 g of 4-dimethylaminopyridine and 25 ml of anhydrous pyridine, with stirring at room temperature. The mixture is stirred for 3 hours at 40° C. and left to cool to room temperature and the whole of it is then poured into 100 ml of a water/ice mixture. After filtration, the residue is washed with copious amounts of distilled water, then with 0.5N hydrochloric acid and finally once again with distilled water. The residue is dissolved in acetone, from which 3.45 g (93%) of 5-methyl-3-(4-methylpyridin-2-yl)-2H,5H-1,3-oxazino[5,6-c][1,2]benzothiazine-2,4-(3H)-dione 6,6-dioxide crystallize with a melting point of 259°–261° C.

Spectroscopic data: IR (KBr): 1195, 1360; 1415; 1640; 1720; 1795 cm$^{-1}$. $^1$H NMR, δ, [DMSO-d$_6$]: 2.42 (s, 3H); 3.10 (s, 3H); 7.40 (m, 2H); 7.98 (m, 4H); 8.40 (d, 1H).

EXAMPLE 4

Preparation of
5-methyl-3-(6-methylpyridin-2-yl)-2H,5H-1,3-oxazino[5,6-c][1,2]benzothiazine-2,4-(3H)-dione 6,6-dioxide 3 ml (0.04 mol) of methyl chloroformate are added dropwise to a partial solution of 3.45 g (0.01 mol) of N-(6-methylpyridin-2-yl)-4-hydroxy-2-methyl-2H-1,2-benzothiazine-3-carboxamide 1,1-dioxide in 2 g of 4-dimethylaminopyridine and 25 ml of anhydrous pyridine, with stirring and with cooling in an ice bath, in such a way that the temperature is always below 10° C. The mixture is stirred for 30 hours at room temperature and the whole of it is poured into 100 ml of a water/ice mixture. After filtration, the residue is washed with copious amounts of distilled water, then with 0.5N hydrochloric acid and finally once again with distilled water. The residue is dissolved in acetone, from which 3.6 g (97%) of 5-methyl-3-(6-methylpyridin-2-yl)-2H,5H-1,3-oxazino[5,6-c][1,2]benzothiazine-2,4-(3H)-dione 6,6-dioxide crystallize with a melting point of 248°–250° C.

Spectroscopic data: IR (KBr): 1190, 1360; 1410; 1640; 1715; 1790 cm$^{-1}$. $^1$H NMR, δ, [DMSO-d$_6$]: 2.43 (s, 3H); 3.00 (s, 3H); 7.40 L (m, 2H); 7.97 (m, 5H).

What is claimed is:

1. A process for the preparation of a 5-methyl-3-heteroaryl-2H,5H-1,3-oxazino-[5,6-c[1,2]benzothiazine-2,4-(3H)-dione 6,6 dioxide of the formula I:

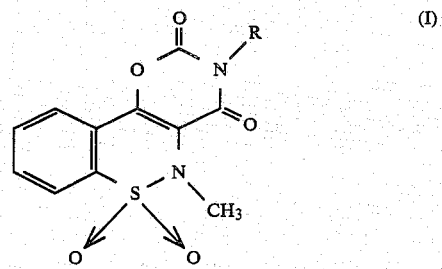

in which R represents a pyrimidinyl or pyridyl group, consisting in reaction an amide of the general formula II:

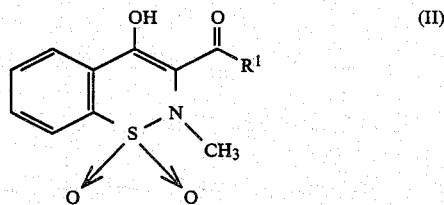

in which $R^1$ represents a pyrimidinylamino or pyridylamino group, with a compound of the general formula III:

in which $R^2$ represents a $C_1$ to $C_4$ lower alkyl radical, an aryl radical or an alkylaryl radical,
wherein the reaction is carried out in an organic solvent selected from the group consisting of pyridine, 4-dimethylaminopyridine, 4-(pyrrolidin-1-yl)pyridine and 2,6-ditert.-butyl-4-methylpyridine, and mixtures thereof.

2. The process as claimed in claim 1, wherein the reaction is carried out in a mixture of pyridines containing 1 to 10% of at least one pyridine selected from the group consisting of 4-dimethylaminopyridine, 4-(pyrrolidin-1-yl)pyridine and 2,6-ditert.-butyl-4-methylpyridine.

3. The process as claimed in claim 1, wherein the reaction temperature is between about −5° C. and about 50° C. for a period of approximately 3 hours to 48 hours.

4. The process as claimed in one of claims 1-3, wherein 5-methyl-3-(pyridin-2-yl)-2H,5H-1,3-oxazino-[5,6-c][1,2]benzothiazine-2,4-(3H)-dione 6,6-dioxide is prepared by reacting an amide of the formula II in which $R^1$ represents pyridin-2-ylamino with a compound of the formula III in which $R^2$ represents the ethyl radical, the reaction being carried out in pyridine, at a temperature of between −5° C. and 40° C., for a period of between 3 hours and 48 hours.

5. The process as claimed in one of claims 1-3, wherein 5-methyl-3-(pyrimidin-2-yl)-2H,5H-1,3-oxazino-[5,6-c][1,2]benzothiazine-2,4-(3H)-dione 6,6-doxide is prepared by reacting an amide of the formula II in which $R^1$ represents pyrimidin-2-ylamino with a compound of the formula III in which $R^2$ represents the benzyl radical, the reaction being carried out in pyridine, at a temperature of between −5° C. and 40° C., for a period of between 3 hours and 48 hours.

6. The process as claimed in one of claims 1-3, wherein 5-methyl-3-(4-methylpyridin-2-yl)-2H,5H-1,3-oxazino-[5,6-c][1,2]benzothiazine-2,4(3H)-dione 6,6-dioxide is prepared by reacting an amide of the formula II in which $R^1$ represents 4-methylpyridin-2-ylamino with a compound of the formula III in which $R^2$ represents the phenyl radical, the reaction being carried out in 4-dimethylaminopyridine and pyridine, at a temperature of between −5° C. and 40° C., for a period of between 3 hours and 48 hours.

7. The process as claimed in one of claims 1-3, wherein 5-methyl-3-(6-methylpyridin-2-yl)-2H,5H-1,3-oxazino-[5,6-c[1,2]benzothiazine-2,4(3H)-dione 6,6-dioxide is prepared by reacting an amide of the formula II in which $R^1$ represents 6-methylpyridin-2-ylamino with a compound of the formula III in which $R^2$ represents the methyl radical, the reaction being carried out in 4-dimethylaminopyridine and pyridine, at a temperature of between −5° C. and 40° C., for a period of between 3 hours and 48 hours.

* * * * *